US012184218B2

United States Patent
Lewis et al.

(10) Patent No.: US 12,184,218 B2
(45) Date of Patent: Dec. 31, 2024

(54) SYSTEM, APPARATUS, AND METHOD FOR A PUMP MOTOR FAILSAFE

(71) Applicant: Hydrocision, Inc., North Billerica, MA (US)

(72) Inventors: Mark Lewis, Haverhill, MA (US); David E. Cassidy, Chelmsford, MA (US)

(73) Assignee: HydroCision, Inc., North Billerica, MA (US)

( * ) Notice: Subject to any disclaimer, the term of this patent is extended or adjusted under 35 U.S.C. 154(b) by 386 days.

(21) Appl. No.: 17/522,854

(22) Filed: Nov. 9, 2021

(65) Prior Publication Data
US 2022/0149759 A1 May 12, 2022

Related U.S. Application Data

(60) Provisional application No. 63/111,137, filed on Nov. 9, 2020.

(51) Int. Cl.
*H02P 6/12* (2006.01)
*H02P 29/10* (2016.01)
(Continued)

(52) U.S. Cl.
CPC ............... *H02P 6/12* (2013.01); *H02P 29/10* (2016.02); *H02P 29/60* (2016.02); *A61M 1/80* (2021.05)

(58) Field of Classification Search
CPC ............ A61M 1/72; A61M 1/80; A61M 3/02; A61M 3/58; A61M 3/0201;
(Continued)

(56) References Cited

U.S. PATENT DOCUMENTS 3,010,401 A * 11/1961 Grandqvist ............ H02K 11/25
310/68 C
4,983,901 A * 1/1991 Lehmer ................ G05B 19/106
318/685
(Continued)

FOREIGN PATENT DOCUMENTS

WO 2017048733 A1 3/2017

OTHER PUBLICATIONS

International Search Report and Written Opinion of the International Searching Authority in relation to international application No. PCT/US2021/058676, dated Feb. 10, 2022, 6 pages.

*Primary Examiner* — Devon C Kramer
*Assistant Examiner* — Joseph S. Herrmann
(74) *Attorney, Agent, or Firm* — Bochner PLLC; Andrew D. Bochner; Eric R. Kleinertz (57) ABSTRACT

Provided for may be a pump failsafe apparatus for use with a pump motor, the pump failsafe apparatus comprising a foot pedal configured to generate a first signal when depressed and a second signal when released. The apparatus may comprise a power supply having an internal logic controlled power switch, the power supply in electrical communication with at least the pump motor, wherein the internal logic controlled power switch includes an active state (ON) and an inactive state (OFF). The apparatus may further include an overspeed detector, an under voltage detector in electrical communication with at least the power supply, the under voltage detector configured to measure a logic voltage, and a pump cartridge detector.

18 Claims, 6 Drawing Sheets

(51) Int. Cl.
*H02P 29/60* (2016.01)
*A61M 1/00* (2006.01)

(58) Field of Classification Search
CPC ........ A61M 2205/14; A61M 2205/121; A61M 2205/3553; A61M 2205/3584; A61M 2205/6018; A61M 2205/6054; F04B 49/20; F04B 49/065; F04B 2201/0201; F04B 2203/0205; F04B 51/00; H02P 6/08; H02P 6/12; H02P 29/10; H02P 29/60; H02K 11/25
USPC ....................................................... 310/68 C
See application file for complete search history.

(56) References Cited

U.S. PATENT DOCUMENTS

| | | | | |
|---|---|---|---|---|
| 10,690,130 | B2* | 6/2020 | Takeuchi | F04B 41/02 |
| 2003/0018252 | A1* | 1/2003 | Duchon | A61M 5/172 |
| | | | | 600/432 |
| 2008/0018281 | A1* | 1/2008 | Kim | H02P 6/12 |
| | | | | 318/268 |
| 2017/0037844 | A1* | 2/2017 | Takeuchi | F04B 49/10 |
| 2018/0309402 | A1* | 10/2018 | Yoshida | B60L 3/003 |
| 2019/0336375 | A1 | 11/2019 | Ferno-Washington | |
| 2019/0351131 | A1* | 11/2019 | Butterfield | A61M 5/14216 |

\* cited by examiner

SYSTEM, APPARATUS, AND METHOD FOR A PUMP MOTOR FAILSAFE

CLAIM OF PRIORITY

This application claims priority from U.S. Provisional Patent Application No. 63/111,137, filed on Nov. 9, 2020, the contents of which are incorporated herein by reference.

FIELD OF THE INVENTION

The present disclosure relates to a medical device. More specifically, the present disclosure relates to a pump failsafe apparatus for use with medical devices that utilize pump motors.

INTRODUCTION

Pumps and pump technology have been used in various applications since nearly the beginning of civilization. In 2000 BC, Egyptians used a very primitive system of pump that was no more sophisticated than a bucket used to raise water from wells. Today, modern industries have come to advance and use pump technology in a myriad of complex ways.

In particular, modern pumps have widespread usage in the field of medical procedures and research. Often a medical professional is required to quickly and effectively removing hazardous material from a patient's body. In such an instance, a mechanical device, such as a pump is needed. The benefit of many of the pumps used in hospitals and research facilities is that they rapidly and precisely remove material. Furthermore, the return pipe of these pumps safely and expediently siphons the unwanted material into a waste collection system where the unwanted material may be properly disposed of.

Although pump technology has advanced significantly since the days of the ancient Egyptians, there are a number of flaws embedded in the modern pump. Often, it is quite difficult to regulate the speed at which a pump and its motor operate. Thus, one pump may be too powerful for a particular application and too weak for another.

Additionally, many modern pumps leave the operator with the difficult task of trying to precisely move the intake of the pump, perhaps within the human body, while the pump is still violently siphoning. Effectively, an operator must use extreme caution when putting the pump intake into the target location because the pump is operating at a speed that will remove any material, wanted or unwanted, in the vicinity of the pump intake.

Further, pumps that move fluid must be primed prior to, and in between, uses. As a result, it is burdensome for an operator to power down the pump and restart suction. Typically, an operator may power down the pump and then precisely place the pump intake, so that wanted material is not superfluously removed. However, in powering down the pump, the operator will likely cause the pump to lose the pressure differential that creates the siphon. Thus, the pump will need to be both primed and powered on when the pump intake is in the proper location. This will often lead to a violent jerk of the pump or the pump intake when the pump both self-primes and powers up.

It would be desirable, therefore, to provide systems and methods that combat the many drawbacks of the modern pump, especially its use in precise operations. It would be further desirable to provide a pump failsafe apparatus that decreases pump speed to a non-clinically relevant speed when the operator is in the process of precisely placing the pump intake.

It would be yet further desirable to provide a pump failsafe apparatus including a number of components that are designed to prevent malfunctions of the pump by monitoring and disabling power when the temperature or voltage are outside the allowed threshold.

SUMMARY

The invention of the present disclosure may be a pump failsafe apparatus for use with a pump motor, the pump failsafe apparatus comprising a pump cartridge configured to connect to the pump motor, and a foot pedal configured to generate a first signal when depressed by a user and a second signal when released by the user. The apparatus may further comprise a power supply comprising an internal logic controlled power switch, the power supply in electrical communication with at least the pump motor, wherein the internal logic controlled power switch includes an active state (ON) and an inactive state (OFF), and wherein the active state and the inactive state are switchable. Further, the apparatus may include an overspeed detector in electrical communication with at least the pump motor and a hall position sensor, the overspeed detector configured to generate a first overspeed signal, the overspeed detector further configured to generate a second overspeed signal, and an under voltage detector in electrical communication with at least the power supply, the under voltage detector configured to measure a logic voltage, the under voltage detector further configured to generate an under voltage disable signal. In an embodiment, the apparatus comprises a pump cartridge detector in electrical communication with at least the pump cartridge, the pump cartridge detector configured to generate a positive pump cartridge signal, the pump cartridge detector further configured to generate a negative pump cartridge signal.

BRIEF DESCRIPTION OF THE DRAWINGS

The incorporated drawings, which are incorporated in and constitute a part of this specification exemplify the aspects of the present disclosure and, together with the description, explain and illustrate principles of this disclosure.

DETAILED DESCRIPTION

For this disclosure, singular words should be construed to include their plural meaning, unless explicitly stated otherwise. Additionally, the term "including" is not limiting. Further, "or" is equivalent to "and/or," unless explicitly stated otherwise. Although, ranges may be stated as preferred, unless stated explicitly, there may exist embodiments that operate outside of preferred ranges.

It is noted that description herein is not intended as an extensive overview, and as such, concepts may be simplified in the interests of clarity and brevity.

All documents mentioned in this application are hereby incorporated by reference in their entirety. Any process described in this application may be performed in any order and may omit any of the steps in the process. Processes may also be combined with other processes or steps of other processes.

Figure 1:
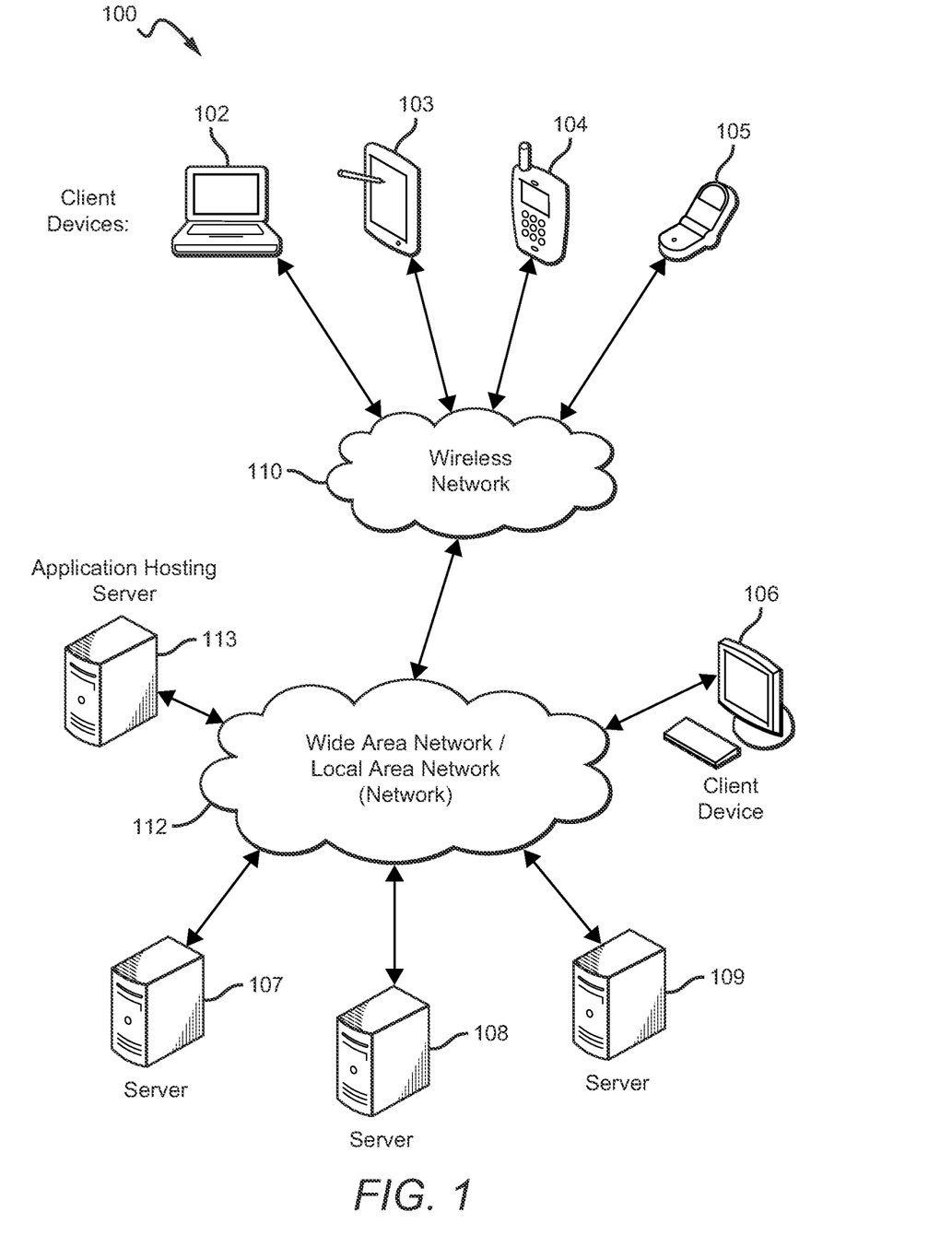
FIG. 1 illustrates a block diagram of a distributed computer system that can implement one or more aspects of an embodiment of the present invention.

FIG. 1 illustrates components of one embodiment of an environment in which the invention may be practiced. Not all of the components may be required to practice the invention, and variations in the arrangement and type of the components may be made without departing from the spirit or scope of the invention. As shown, the system 100 includes one or more Local Area Networks ("LANs")/Wide Area Networks ("WANs") 112, one or more wireless networks 110, one or more wired or wireless client devices 106, mobile or other wireless client devices 102-105, servers 107-109, and may include or communicate with one or more data stores or databases. Various of the client devices 102-106 may include, for example, desktop computers, laptop computers, set top boxes, tablets, cell phones, smart phones, smart speakers, wearable devices (such as the Apple Watch) and the like. Servers 107-109 can include, for example, one or more application servers, content servers, search servers, and the like. FIG. 1 also illustrates application hosting server 113.

Figure 2:
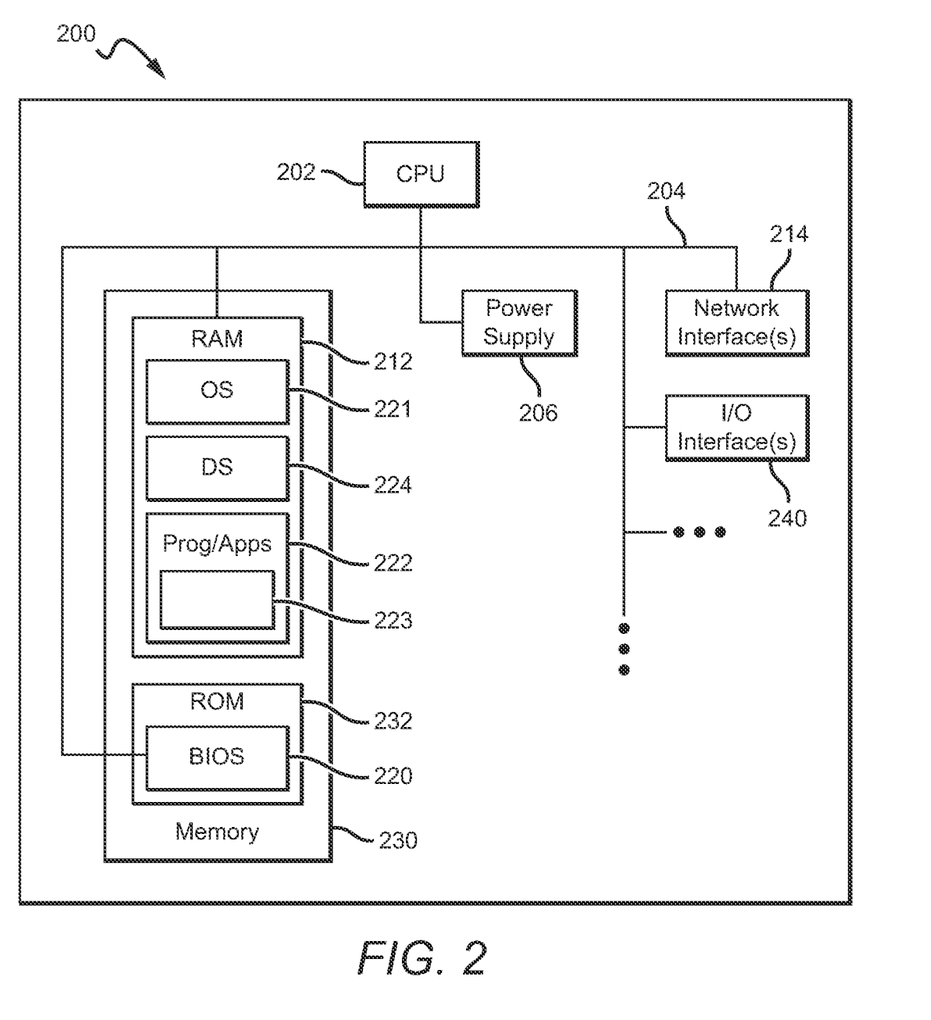
FIG. 2 illustrates a block diagram of an electronic device that can implement one or more aspects of an embodiment of the invention.

FIG. 2 illustrates a block diagram of an electronic device 200 that can implement one or more aspects of an apparatus, system and method for increasing mobile application user engagement (the "Engine") according to one embodiment of the invention. Instances of the electronic device 200 may include servers, e.g., servers 107-109, and client devices, e.g., client devices 102-106. In general, the electronic device 200 can include a processor/CPU 202, memory 230, a power supply 206, and input/output (I/O) components/devices 240, e.g., microphones, speakers, displays, touchscreens, keyboards, mice, keypads, microscopes, GPS components, cameras, heart rate sensors, light sensors, accelerometers, targeted biometric sensors, etc., which may be operable, for example, to provide graphical user interfaces or text user interfaces.

A user may provide input via a touchscreen of an electronic device 200. A touchscreen may determine whether a user is providing input by, for example, determining whether the user is touching the touchscreen with a part of the user's body such as his or her fingers. The electronic device 200 can also include a communications bus 204 that connects the aforementioned elements of the electronic device 200. Network interfaces 214 can include a receiver and a transmitter (or transceiver), and one or more antennas for wireless communications.

The processor 202 can include one or more of any type of processing device, e.g., a Central Processing Unit (CPU), and a Graphics Processing Unit (GPU). Also, for example, the processor can be central processing logic, or other logic, may include hardware, firmware, software, or combinations thereof, to perform one or more functions or actions, or to cause one or more functions or actions from one or more other components. Also, based on a desired application or need, central processing logic, or other logic, may include, for example, a software-controlled microprocessor, discrete logic, e.g., an Application Specific Integrated Circuit (ASIC), a programmable/programmed logic device, memory device containing instructions, etc., or combinatorial logic embodied in hardware. Furthermore, logic may also be fully embodied as software.

The memory 230, which can include Random Access Memory (RAM) 212 and Read Only Memory (ROM) 232, can be enabled by one or more of any type of memory device, e.g., a primary (directly accessible by the CPU) or secondary (indirectly accessible by the CPU) storage device (e.g., flash memory, magnetic disk, optical disk, and the like). The RAM can include an operating system 221, data storage 224, which may include one or more databases, and programs and/or applications 222, which can include, for example, software aspects of the program 223. The ROM 232 can also include Basic Input/Output System (BIOS) 220 of the electronic device.

Software aspects of the program 223 are intended to broadly include or represent all programming, applications, algorithms, models, software and other tools necessary to implement or facilitate methods and systems according to embodiments of the invention. The elements may exist on a single computer or be distributed among multiple computers, servers, devices or entities.

The power supply 206 contains one or more power components, and facilitates supply and management of power to the electronic device 200.

The input/output components, including Input/Output (I/O) interfaces 240, can include, for example, any interfaces for facilitating communication between any components of the electronic device 200, components of external devices (e.g., components of other devices of the network or system 100), and end users. For example, such components can include a network card that may be an integration of a receiver, a transmitter, a transceiver, and one or more input/output interfaces. A network card, for example, can facilitate wired or wireless communication with other devices of a network. In cases of wireless communication, an antenna can facilitate such communication. Also, some of the input/output interfaces 240 and the bus 204 can facilitate communication between components of the electronic device 200, and in an example can ease processing performed by the processor 202.

Where the electronic device 200 is a server, it can include a computing device that can be capable of sending or receiving signals, e.g., via a wired or wireless network, or may be capable of processing or storing signals, e.g., in memory as physical memory states. The server may be an application server that includes a configuration to provide one or more applications, e.g., aspects of the Engine, via a network to another device. Also, an application server may, for example, host a web site that can provide a user interface for administration of example aspects of the Engine.

Any computing device capable of sending, receiving, and processing data over a wired and/or a wireless network may act as a server, such as in facilitating aspects of implementations of the Engine. Thus, devices acting as a server may include devices such as dedicated rack-mounted servers, desktop computers, laptop computers, set top boxes, integrated devices combining one or more of the preceding devices, and the like.

Servers may vary widely in configuration and capabilities, but they generally include one or more central processing units, memory, mass data storage, a power supply, wired or wireless network interfaces, input/output interfaces, and an operating system such as Windows Server, Mac OS X, Unix, Linux, FreeBSD, and the like.

A server may include, for example, a device that is configured, or includes a configuration, to provide data or content via one or more networks to another device, such as in facilitating aspects of an example apparatus, system and method of the Engine. One or more servers may, for example, be used in hosting a Web site, such as the web site www.microsoft.com. One or more servers may host a variety of sites, such as, for example, business sites, informational sites, social networking sites, educational sites, wikis, financial sites, government sites, personal sites, and the like.

Servers may also, for example, provide a variety of services, such as Web services, third-party services, audio services, video services, email services, HTTP or HTTPS services, Instant Messaging (IM) services, Short Message Service (SMS) services, Multimedia Messaging Service (MMS) services, File Transfer Protocol (FTP) services, Voice Over IP (VOIP) services, calendaring services, phone services, and the like, all of which may work in conjunction with example aspects of an example systems and methods for the apparatus, system and method embodying the Engine. Content may include, for example, text, images, audio, video, and the like.

In example aspects of the apparatus, system and method embodying the Engine, client devices may include, for example, any computing device capable of sending and receiving data over a wired and/or a wireless network. Such client devices may include desktop computers as well as portable devices such as cellular telephones, smart phones, display pagers, Radio Frequency (RF) devices, Infrared (IR) devices, Personal Digital Assistants (PDAs), handheld computers, GPS-enabled devices tablet computers, sensor-equipped devices, laptop computers, set top boxes, wearable computers such as the Apple Watch and Fitbit, integrated devices combining one or more of the preceding devices, and the like.

Client devices such as client devices 102-106, as may be used in an example apparatus, system and method embodying the Engine, may range widely in terms of capabilities and features. For example, a cell phone, smart phone or tablet may have a numeric keypad and a few lines of monochrome Liquid-Crystal Display (LCD) display on which only text may be displayed. In another example, a Web-enabled client device may have a physical or virtual keyboard, data storage (such as flash memory or SD cards), accelerometers, gyroscopes, respiration sensors, body movement sensors, proximity sensors, motion sensors, ambient light sensors, moisture sensors, temperature sensors, compass, barometer, fingerprint sensor, face identification sensor using the camera, pulse sensors, heart rate variability (HRV) sensors, beats per minute (BPM) heart rate sensors, microphones (sound sensors), speakers, GPS or other location-aware capability, and a 2D or 3D touch-sensitive color screen on which both text and graphics may be displayed. In some embodiments multiple client devices may be used to collect a combination of data. For example, a smart phone may be used to collect movement data via an accelerometer and/or gyroscope and a smart watch (such as the Apple Watch) may be used to collect heart rate data. The multiple client devices (such as a smart phone and a smart watch) may be communicatively coupled.

Client devices, such as client devices 102-106, for example, as may be used in an example apparatus, system and method implementing the Engine, may run a variety of operating systems, including personal computer operating systems such as Windows, iOS or Linux, and mobile operating systems such as iOS, Android, Windows Mobile, and the like. Client devices may be used to run one or more applications that are configured to send or receive data from another computing device. Client applications may provide and receive textual content, multimedia information, and the like. Client applications may perform actions such as browsing webpages, using a web search engine, interacting with various apps stored on a smart phone, sending and receiving messages via email, SMS, or MMS, playing games (such as fantasy sports leagues), receiving advertising, watching locally stored or streamed video, or participating in social networks.

In example aspects of the apparatus, system and method implementing the Engine, one or more networks, such as networks 110 or 112, for example, may couple servers and client devices with other computing devices, including through wireless network to client devices. A network may be enabled to employ any form of computer readable media for communicating information from one electronic device to another. The computer readable media may be non-transitory. A network may include the Internet in addition to Local Area Networks (LANs), Wide Area Networks (WANs), direct connections, such as through a Universal Serial Bus (USB) port, other forms of computer-readable media (computer-readable memories), or any combination thereof. On an interconnected set of LANs, including those based on differing architectures and protocols, a router acts as a link between LANs, enabling data to be sent from one to another.

Communication links within LANs may include twisted wire pair or coaxial cable, while communication links between networks may utilize analog telephone lines, cable lines, optical lines, full or fractional dedicated digital lines including T1, T2, T3, and T4, Integrated Services Digital Networks (ISDNs), Digital Subscriber Lines (DSLs), wireless links including satellite links, optic fiber links, or other communications links known to those skilled in the art. Furthermore, remote computers and other related electronic devices could be remotely connected to either LANs or WANs via a modem and a telephone link.

A wireless network, such as wireless network 110, as in an example apparatus, system and method implementing the Engine, may couple devices with a network. A wireless network may employ stand-alone ad-hoc networks, mesh networks, Wireless LAN (WLAN) networks, cellular networks, and the like.

A wireless network may further include an autonomous system of terminals, gateways, routers, or the like connected by wireless radio links, or the like. These connectors may be configured to move freely and randomly and organize themselves arbitrarily, such that the topology of wireless network may change rapidly. A wireless network may further employ a plurality of access technologies including 2nd (2G), 3rd (3G), 4th (4G) generation, Long Term Evolution (LTE) radio access for cellular systems, WLAN, Wireless Router (WR) mesh, and the like. Access technologies such as 2G, 2.5G, 3G, 4G, and future access networks may enable wide area coverage for client devices, such as client devices with various degrees of mobility. For example, a wireless network may enable a radio connection through a radio network access technology such as Global System for Mobile communication (GSM), Universal Mobile Telecommunications System (UMTS), General Packet Radio Services (GPRS), Enhanced Data GSM Environment (EDGE), 3GPP Long Term Evolution (LTE), LTE Advanced, Wideband Code Division Multiple Access (WCDMA), Bluetooth, 802.11b/g/n, and the like. A wireless network may include virtually any wireless communication mechanism by which information may travel between client devices and another computing device, network, and the like.

Internet Protocol (IP) may be used for transmitting data communication packets over a network of participating digital communication networks, and may include protocols such as TCP/IP, UDP, DECnet, NetBEUI, IPX, Appletalk, and the like. Versions of the Internet Protocol include IPv4 and IPV6. The Internet includes local area networks (LANs), Wide Area Networks (WANs), wireless networks, and long-haul public networks that may allow packets to be communicated between the local area networks. The packets may be transmitted between nodes in the network to sites each of which has a unique local network address. A data communication packet may be sent through the Internet from a user site via an access node connected to the Internet. The packet may be forwarded through the network nodes to any target site connected to the network provided that the site address of the target site is included in a header of the packet. Each packet communicated over the Internet may be routed via a path determined by gateways and servers that switch the packet according to the target address and the availability of a network path to connect to the target site.

The header of the packet may include, for example, the source port (16 bits), destination port (16 bits), sequence number (32 bits), acknowledgement number (32 bits), data offset (4 bits), reserved (6 bits), checksum (16 bits), urgent pointer (16 bits), options (variable number of bits in multiple of 8 bits in length), padding (may be composed of all zeros and includes a number of bits such that the header ends on a 32 bit boundary). The number of bits for each of the above may also be higher or lower.

A "content delivery network" or "content distribution network" (CDN), as may be used in an example apparatus, system and method implementing the Engine, generally refers to a distributed computer system that comprises a collection of autonomous computers linked by a network or networks, together with the software, systems, protocols and techniques designed to facilitate various services, such as the storage, caching, or transmission of content, streaming media and applications on behalf of content providers. Such services may make use of ancillary technologies including, but not limited to, "cloud computing," distributed storage, DNS request handling, provisioning, data monitoring and reporting, content targeting, personalization, and business intelligence. A CDN may also enable an entity to operate and/or manage a third party's web site infrastructure, in whole or in part, on the third party's behalf.

A Peer-to-Peer (or P2P) computer network relies primarily on the computing power and bandwidth of the participants in the network rather than concentrating it in a given set of dedicated servers. P2P networks are typically used for connecting nodes via largely ad hoc connections. A pure peer-to-peer network does not have a notion of clients or servers, but only equal peer nodes that simultaneously function as both "clients" and "servers" to the other nodes on the network.

Embodiments of the present invention include apparatuses, systems, and methods implementing the Engine. Embodiments of the present invention may be implemented on one or more of client devices 102-106, which are communicatively coupled to servers including servers 107-109. Moreover, client devices 102-106 may be communicatively (wirelessly or wired) coupled to one another. In particular, software aspects of the Engine may be implemented in the program 223. The program 223 may be implemented on one or more client devices 102-106, one or more servers 107-109, and 113, or a combination of one or more client devices 102-106, and one or more servers 107-109 and 113.

Figure 3:
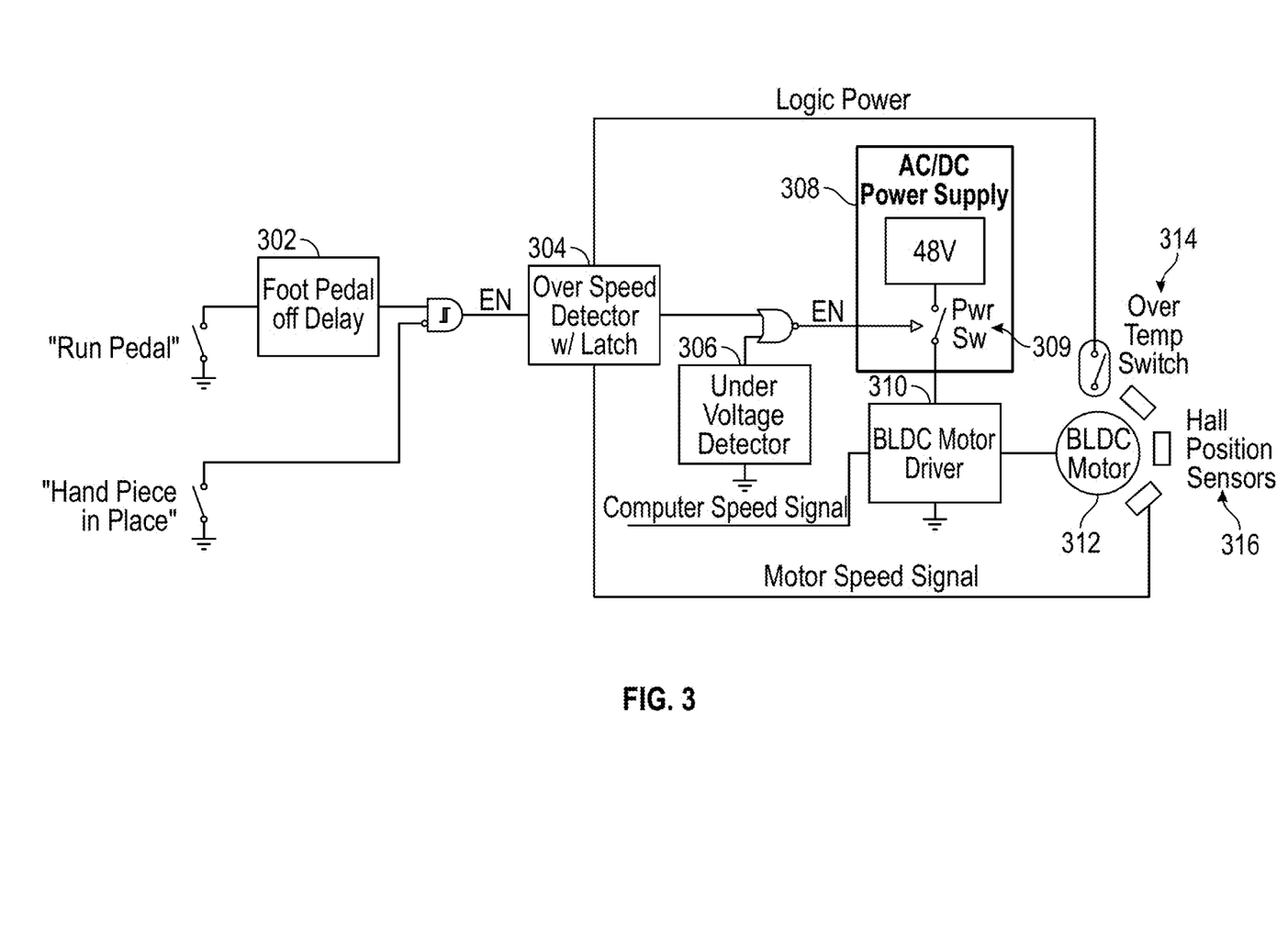
FIG. 3 illustrates a circuit view of a pump failsafe apparatus according to various embodiments of the present disclosure.

FIG. 3 illustrates a circuit view of a pump failsafe apparatus according to an embodiment. In this embodiment, the pump failsafe apparatus may be used in conjunction with a medical device that utilizes a pump or similar apparatus. However, in alternate embodiments, the pump failsafe apparatus is not limited to use with solely medical devices. Further, the pump failsafe apparatus may be paired with any number, or type, of pumps and/or motors.

In an embodiment, the pump failsafe apparatus includes a foot pedal 302, an overspeed detector 304, an under voltage detector 306, a power supply 308, a BLDC motor driver 310, a BLDC motor 312, an over temperature switch 314, and/or a hall position sensor 316.

In a further embodiment, the foot switch 302 is a pedal that may be depressed and/or released by a user. Alternatively, the foot switch 302 may be replaced with a switch operated by a user's hand, a pressure sensitive mat, a vocal command device, or any other controller that is capable of generating at least two signals. In a further alternate embodiment, the pump failsafe apparatus may include one or more foot switches 302. In this further alternate embodiment, the one or more footswitches 302 may be operable by more than one user, may generate different signals, or may be in direct electrical communication with different components of the pump failsafe apparatus. Alternatively, the function of the foot switch 302 may be accomplished by a button or buttons disposed directly on the surface of the apparatus connected to the host machine.

In an embodiment, the foot switch 302 may generate any suitable number of signals, such as two signals. The first signal may be generated when the user depresses the foot switch. The second signal may be generated when the user releases the foot switch. However, there exist alternate embodiments where there are more than two signals. In further embodiments, the first signal and/or the second signal are generated when the user "double clicks" the foot pedal 302. Alternatively, the first signal and/or second signal may be generated when the user holds the foot pedal 302 down for a predetermined period of time.

Further, in an embodiment, the foot pedal 302 enables a pump motor to be run by a computer. In an embodiment, when the foot pedal 302 is depressed, a first signal is generated, the first signal is transmitted to the over speed detector 304. The first signal may disable the overspeed detector 304. In some embodiments, the first signal immediately disables the overspeed detector 304. However, in other embodiments, when the user depresses the foot pedal 302, the foot pedal 302 sends the first signal on a delay, such that the overspeed detector 304 is disabled, but not immediately. This may be achieved in various ways in different embodiments, including, but not limited to, a delay switch embedded in the foot pedal 302, an additional component disposed between the foot pedal 302 and the overspeed detector 304, or a delay switch embedded in the overspeed detector 304. However, there exist alternate embodiments where the overspeed detector 304 is disabled immediately. The delay may be configured such that the pump returns to a specific position. For example, the delay may be configured such that, upon actuating the foot pedal, the piston has a sufficient period of time to return to its appropriate resting state (for example, top dead center [TDC] or bottom dead center [BDC])

In an embodiment, the pump failsafe apparatus includes an overspeed detector 304. The overspeed detector 304, for the purposes of this embodiment, is the first component that the foot pedal 302 communicates with. In an embodiment, the overspeed detector 304 is also in communication with the hall position sensor 316. In alternate embodiments, the pump failsafe apparatus includes more than one hall position sensor 316.

In an embodiment, the overspeed detector 304 measures the pump motor speed utilizing the hall position sensor 316. In an embodiment, the overspeed detector 304 is set at a speed below the clinically relevant speed. Selecting a number from 1 to 10 in the user interface may choose pump speeds. Each number may be associated with the following regulated speeds: 390, 490, 590, 690, 790, 862, 934, 1004, 1078, and/or 1150 TPM (thrusts per minute), or any suitable variation thereof. In some embodiments, 60 TPM, a clinically irrelevant speed, is used to index the transmission at top dead center to facilitate the loading and locking of the pump cartridge. The speed at which the fault detection is triggered may be approximately 100 TPM.

The clinically relevant speed may be the speed of the pump motor that is required to enable a tool or instrument attached to the pump to propel adequate fluid, siphon adequate waste, or other otherwise perform an action in a manner that allows the user to use the medical device for its intended purpose. Conversely, a non-clinically relevant speed may be the speed of the pump motor when the connected tool/handpiece is receiving power, fluid, or pressure, but is not operating at a level sufficient to carry out the purpose of the underlying device.

For example, in an embodiment where the pump motor is connected to a medical siphon, the clinically relevant speed would enable human tissue to be siphoned from the human body and the non-clinically relevant speed would maintain some degree of suction, but not to a degree that is useful in removing human tissue. However, in alternate embodiments, the clinically relevant speed, non-clinically relevant speed, and speed limit are determined by the user and may differ depending on the accompanying device. However, at a non-clinically relevant speed, the pump may continue to run, while the function of the handpiece/tool is unnoticeable.

In an embodiment where the suction is never completely ceased, the pump need not be re-primed, and neither the pump nor pump intake experiences the violent jerking associated with starting an unprimed pump. However, there are embodiments where the user may manually prime the pump. In alternate embodiments, the user may prime the pump by depressing or releasing the foot pedal 302 or actuating another button, lever, or switch. In further embodiments, the pump failsafe apparatus may include an additional component configured to detect when the pump must be primed. The apparatus may automatically prime the pump when a sensor detects that a pump is not primed. In such an embodiment, a priming sensor may be in communication with the computer, processor, pump motor, or another component that is configured to prime the pump.

In an embodiment, there is priming identification built into the system. When a user starts a procedure, the software will instruct the user to prime the unit first. The system may not allow the user to progress until it has been identified that the pump has been primed. The system may identify whether the pump is primed by monitoring the electrical system. For example, the act of priming or operation of a pre-primed pump may draw a higher voltage. Accordingly, the system may be configured to determine when a voltage profile is indicative of a primed versus unprimed pump. For example, when the pump is primed, the pump may draw a reduced level of voltage. Thus, the system may utilize the motor's drawn voltage to determine whether the pump is primed. The warning to the user may be displayed on a computer monitor or the apparatus' interface.

Further, an embodiment includes a pump cartridge detector. In this embodiment, the pump cartridge detector determines whether a pump cartridge is in proper communication with the pump motor or other component of the host device. In an embodiment, the pump cartridge detector is configured to determine when the pump cartridge is in a position that enables the automatic locking process.

Locking the pump cartridge in place may incorporate a plurality of steps. In some embodiments, the position of the piston in the pump cartridge, although initialized in manufacturing, cannot be guaranteed. The first step may be to force the pump cartridge piston into a known location. This is accomplished by, for example, first positioning the transmission at top dead center (piston fully compressed) before the pump cartridge is inserted. Thus, the pump motor may be turned at 60 TPM until the index sensor detects the proper position. When the pump cartridge is inserted, the piston may first bottom out on the transmission drive shaft. Multiple optical sensors may be mounted in an array at the inlet of the transmission specific to detecting the pump cartridge location and its motion. The optical sensors may be coupled with software to detect the motion of the cartridge going into the nest. If the piston position is not fully compressed and the cartridge motion stops, the user interface may indicate to the user to continue pushing the pump cartridge, compressing the piston until it is fully compressed and the mechanical locking features align with the pump cartridge attributes. Two mechanical attributes may hold the pump cartridge in place. A first feature may be a guillotine that holds the body (cylinder) of the cartridge in a fixed location. The guillotine may take all the compression force of the pump. A comb may lock the piston shaft to the transmission drive shaft. In some embodiments, a slot in the piston shaft, holes in the transmission driveshaft, and pins of the comb need to align for the comb to be slid into the lock position. In some embodiments, force during pumping is only applied to the comb when the piston is retracted, such as when fluid is being siphoned from the fluid source.

Further, when the pump cartridge detector detects that the pump cartridge is in a position to enable the automatic locking process, the pump cartridge detector generates a positive signal. Moreover, in an embodiment, if the pump cartridge detector does not detect that the pump cartridge is in the proper position, the pump cartridge detector generates a negative signal.

In an embodiment a positive signal from the pump cartridge detector enables the pump motor to function, allows the power supply 308 to disseminate power to other components, or enables the apparatus to function in some other way. In further embodiments, the pump cartridge detector operates on a delay, such that a negative signal does not immediately stop the pump motor. In an embodiment, a negative signal from the pump cartridge detector would stop the pump motor slowly or on a delay.

For the purposes of this disclosure, reference to "stopping" the motor may refer to decreasing the motor speed to a non-clinically relevant speed or to a complete stop. For example, an active state may refer to the pump motor operating a clinically relevant speed and an inactive state may refer to the pump motor operating at a non-clinically relevant speed.

In an embodiment, the overspeed detector 304 is enabled by the second signal (for example, the foot pedal 302 being released) and a positive signal from the pump cartridge detector (for example, the pump cartridge is in proper communication with the pump, pump motor, or host device). However, there exist alternative embodiments where the pump failsafe apparatus operates without the pump cartridge detector. In embodiments that include a pump cartridge detector, the pump cartridge detector may determine proper placement of the pump cartridge via a pressure switch, electrical switch, infrared sensor, or other proximity sensor. In an embodiment, the pump cartridge detector is an optical sensor. Further, in an embodiment, the operator is notified of the pump cartridge's position. The pump cartridge position may be located relative to the nest containing the locking mechanism. Optical sensors and software may monitor the motion of the cartridge as it is inserted into the nest, to determine when it is in the proper position for locking. If the optical sensor that detects the barrel of the pump cartridge is occluded, the fault circuit may be enabled independent of the lock. This feature may allow the pump to be run independently of the handpiece cartridge being in place.

In an embodiment, if the overspeed detector 304 operates improperly or is otherwise experiencing an error, the user may reset the overspeed detector 304 by depressing the foot pedal 302 (first signal) again. Also in an embodiment, the overspeed detector 304 receives power and/or communication from an over temperature switch 314. In certain embodiments, the apparatus is specifically constructed to run at an ambient temperature between 4 and 38 degrees Celsius. The motor over temperature switch 314 may be set to 75 degrees Celsius. A secondary thermistor may be used by the computer to monitor the motor's temperature. The over temperature switch 314 may be disposed anywhere in the pump failsafe apparatus, however, in an embodiment, the over temperature switch 314 may be connected to the system's logic power such that power is discontinued in case of an overheating motor. However, there may exist embodiments where the pump failsafe apparatus does not require an over temperature switch 314. In alternate embodiments, the over temperature switch 314 can detect the temperature of other components of the pump failsafe apparatus, for example, the temperature of the pump cartridge or power supply 308.

The system may include any number of thermistors and/or temperature sensors. For example, one temperature sensor may be configured to monitor the motor temperature, while another may be configured to monitor the ambient temperature, and another may be configured to monitor the logic temperature. Thus, each temperature sensor and/or thermistor may be associated with a location or system component, and each sensor and/or thermistor may have a different threshold temperature. For example, the motor temperature may have a higher threshold temperature than the ambient temperature.

Figure 4:
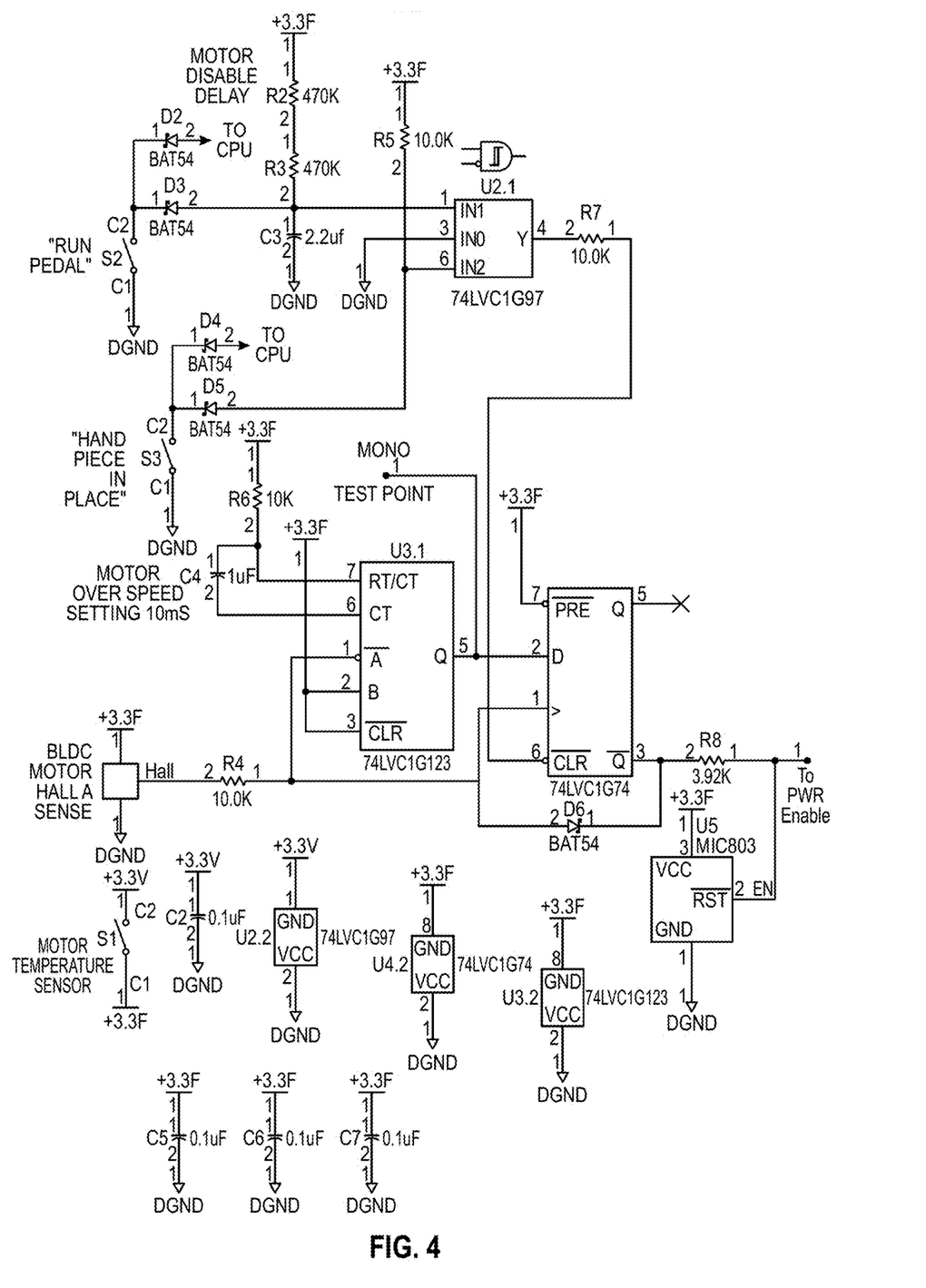
FIG. 4 illustrates a circuit view of a pump failsafe apparatus according to various embodiments of the present disclosure.

Further, in an embodiment, the pump failsafe apparatus includes an under voltage detector 306. The under voltage detector 306 in FIG. 3 may monitor the logic voltage. Referring to FIG. 4, this may be measured by a UI 1. 3.3 Volt logic supply, which may pass through the motor over temperature switch 314. When the motor over temperature switch 314 in FIG. 3 is conducting the UI 1, a supply supervisor IC may monitor the supply voltage. For the purposes of various embodiments, if the logic voltage falls below the voltage necessary for proper operation, the under voltage detector 306 generates a signal disabling the pump, motor, or power supply 308 in FIG. 3. In various embodiments, the under voltage detector 306 disables the pump in various ways, including, but not limited to, sending a signal to the power supply 308 to power down or operate the pump at a non-clinical speed, sending a signal to the power supply 308 to instruct the power supply to no longer send power to the pump motor, or to send a signal to another component disposed between the power supply 308 and the pump motor that can interrupt the flow of power (for example, a computer and/or processor).

In some embodiments the power supply 308 is an AC/DC power supply. However, in alternate embodiments, various power supplies commonly known may be used. In many embodiments, the power supply 308 further includes an internal logic controlled power switch 309. In an embodiment, the internal logic controller power switch may enable and disable power output by the power supply 308. Further, the internal logic controlled power switch 309 may disable the flow of power from the power supply 308 when both the over speed detector 304 and the under voltage detector 306 generate signals. In such an embodiment, for example, the power supply 308 may output power when the pump motor is operating below the speed limit and the logic temperature is below the approved threshold. However, in alternate embodiments, a positive signal from only one detector (for example, detectors 304/306/314) may be sufficient to actuate the internal logic controlled power switch 309.

An embodiment also includes a brushless DC motor ("BLDC") 312 and a BLDC motor driver 310. In such an embodiment, the BLDC motor driver 310 applies power from the power supply 308 to the BLDC 312. However, there exist other embodiments where the pump failsafe apparatus includes a brushed DC motor. In an embodiment, the BLDC motor driver 310 contains the logic necessary to convert the signals from the computer speed signal and the signals from the hall position monitor 316 into an AC voltage that drives the pump motor. In many embodiments, the computer speed signal is a signal that directs the pump motor how fast to operate. The computer speed signal may originate from elsewhere within the apparatus, within the host device, or the computer speed signal may be directly input by the user.

In other embodiments, the pump failsafe apparatus includes a tool/handpiece sensor. In some embodiments, the tool sensor is configured to determine the type of tool that is receiving fluid or power from the pump. For example, in one embodiment, the tool sensor determines whether either a siphon or a powered cutting instrument is connected to the pump. In further embodiments, the tool sensor determines whether the tool is properly connected to the pump. For example, in one embodiment, the tool sensor determines whether a powered cutting instrument is installed flush to the tube or handpiece connection interface.

There exist embodiments where the computer or the memory includes a spreadsheet where the spreadsheet is populated by a list of tools/handpieces and the preferred corresponding settings for each tool. For example, in this embodiment, the spreadsheet may indicate that a particular tool requires a certain power output, pump speed, duration, or other characteristics. In further embodiments, the memory contains computer-executable instructions that instruct the processor how to adjust the pump motor or other components of the host device to tailor the pump motor to the connected tool.

In further embodiments, the tool sensor may generate a signal and may distribute that signal to the computer or other components of the pump failsafe apparatus. In such embodiments, if the tool is not properly installed, this signal may instruct the computer, or the power supply directly, that the power supply must stop distributing power to the pump motor (or at least operate at a non-clinically relevant speed) or other components of the apparatus.

Figure 5:
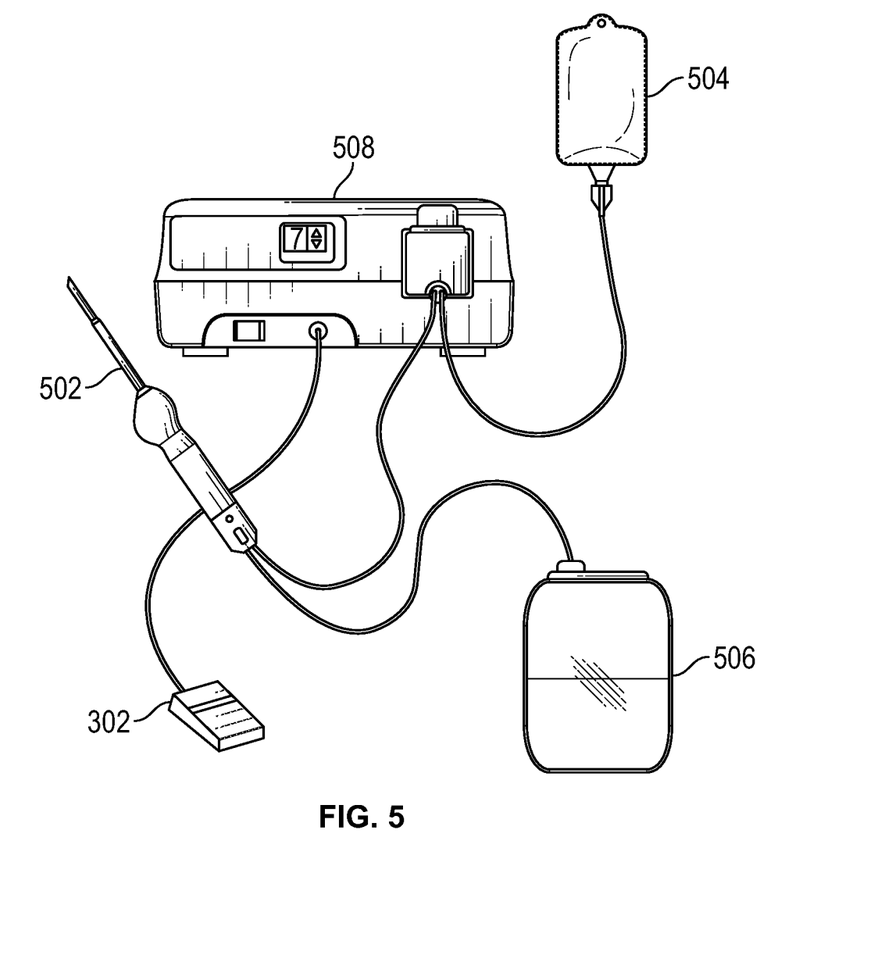
FIG. 5 illustrates an embodiment of the pump failsafe apparatus in use with a medical device.

Referring to FIG. 5, the pump failsafe apparatus may be utilized in a system having a foot pedal 302, a hand piece 502, a saline bag 504, a waste container 506, and/or a power console 508. The power console 508 may house the pump and computer components of the pump failsafe apparatus. The foot pedal 302 and/or the hand piece 502 may be in electrical communication with the pump failsafe apparatus, such that signals generated by the foot pedal 302 and/or hand piece 502 may influence the operation of the pump failsafe apparatus. However, the pump failsafe apparatus may be used in conjunction with any number or combination of devices.

The apparatus may be equipped with a sensor configured to determine the identity of the handpiece. For example, each handpiece may include a magnetic location on the flange of the handpiece, where the magnetic location is configured to be recognized by the console itself. The console or the cable connecting the console to the handpiece may include a sensor configured to read the flange or magnetic portion of the handpiece. Accordingly, depending on which handpiece is identified the apparatus may adjust the settings (for example, motor speed). Such a determination and adjustment may be made by the software and system as a whole. In a further embodiment, the user may have the ability to override the system's selection and choose a different motor speed setting (for example, 1-10) via the user interface.

The invention of the present disclosure may be a pump failsafe apparatus for use with a pump motor, the pump failsafe apparatus comprising a pump cartridge configured to connect to the pump motor, and a foot pedal configured to generate a first signal when depressed by a user and a second signal when released by the user. The apparatus may further comprise a power supply comprising an internal logic controlled power switch, the power supply in electrical communication with at least the pump motor, wherein the internal logic controlled power switch includes an active state (ON) and an inactive state (OFF), and wherein the active state and the inactive state are switchable. Further, the apparatus may include an overspeed detector in electrical communication with at least the pump motor and a hall position sensor, the overspeed detector configured to generate a first overspeed signal, the overspeed detector further configured to generate a second overspeed signal, and an under voltage detector in electrical communication with at least the power supply, the under voltage detector configured to measure a logic voltage, the under voltage detector further configured to generate an under voltage disable signal. In an embodiment, the apparatus comprises a pump cartridge detector in electrical communication with at least the pump cartridge, the pump cartridge detector configured to generate a positive pump cartridge signal, the pump cartridge detector further configured to generate a negative pump cartridge signal.

In an embodiment, the pump failsafe apparatus further comprises an over temperature switch in electrical communication with at least the overspeed detector, where the over temperature switch is configured to determine a motor temperature and to instruct the apparatus to enter the inactive state if the motor temperature surpasses a predetermined motor temperature threshold. The predetermined motor temperature threshold may be 75 degrees Celsius. In a further embodiment, the apparatus includes a thermistor configured to monitor the motor temperate and/or an ambient temperature of the apparatus or underlying device.

The pump failsafe apparatus may further comprise a handpiece sensor in electrical communication with at least the overspeed detector, where the handpiece sensor is configured to determine whether a handpiece is properly attached and, if the handpiece is not properly attached, to instruct the apparatus to enter the inactive state. In an embodiment, the first signal, generated upon depression of the foot pedal, immediately disables the overspeed detector, and the second signal, generated upon release of the foot pedal, includes a delay, enabling the pump motor to slow from a clinically relevant speed to a non-clinically relevant speed. In an embodiment, the pump cartridge detector is configured to determine whether the pump cartridge is in proper communication with the pump motor, where a pump cartridge piston is forced into a known location by positioning a transmission at a top dead center position before fully inserting the pump cartridge, where the pump motor is turned to 60 thrusts per minute, enabling an index sensor to detect a position of the pump cartridge piston, and/or where, if the piston position is not fully compressed and the pump cartridge motion stops, a user interface generates a warning to the user until the pump cartridge piston is fully compressed.

The pump cartridge detector may be one or more optical sensors (for example, a series of optical sensors). In one embodiment, the pump motor is a brushless DC motor, and the pump motor is in electrical communication with a motor driver, where the motor driver is configured to transfer power from the power supply to the pump motor. The motor driver may be further configured to convert a computer speed signal and signals from the hall position motor into an AC voltage.

Figure 6:
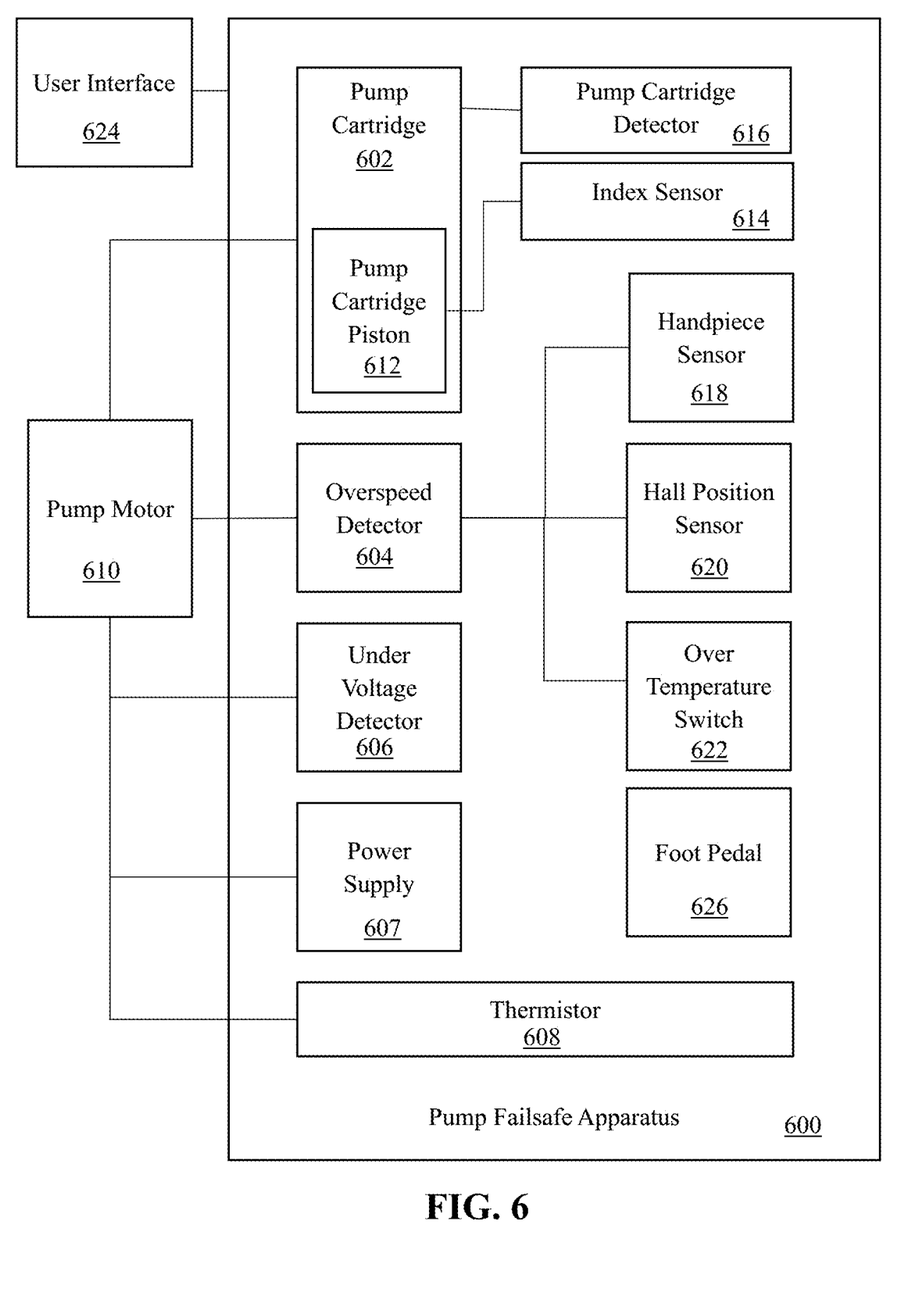
FIG. 6 illustrates a block diagram of the pump failsafe apparatus in connection with the pump motor according to an embodiment of the invention.

FIG. 6 illustrates a block diagram of one or more aspects of a pump failsafe apparatus 600. The pump failsafe apparatus 600 comprises a pump cartridge 602, an overspeed detector 604, an under voltage detector 606, a power supply 607, and a thermistor 608, each in communication with a pump motor 610. The pump failsafe apparatus 600 may further comprise a foot pedal 626. As illustrated, the pump cartridge 602 comprises a pump cartridge piston 612. An index sensor 614 may detect a position of the pump cartridge piston 612, for example, when the pump cartridge piston 612 is fully compressed and a transmission is located at a top dead center position. The pump cartridge 602 may be in electrical communication with a pump cartridge detector 616 and may detect whether the pump cartridge 602 is in proper communication with the pump motor 610. The overspeed detector 604 may be in communication with a handpiece sensor 618, a hall position sensor 620, and an over temperature switch 622. The pump failsafe apparatus 600 may be in further communication with a user interface 624, wherein, in some instances, the user interface 624 may generate a warning. Any of the components discussed with reference to FIG. 6 may comprise any of the characteristics discussed herein.

While this invention has been described in conjunction with the embodiments outlined above, many alternatives, modifications and variations will be apparent to those skilled in the art upon reading the foregoing disclosure. Accordingly, the embodiments of the invention, as set forth above, are intended to be illustrative, not limiting. Various changes may be made without departing from the spirit and scope of the invention.

What is claimed is:

1. A pump failsafe apparatus for use with a pump motor, the pump failsafe apparatus comprising:
- a pump cartridge configured to connect to the pump motor;
- a foot pedal configured to generate a first signal when depressed by a user, the foot pedal further configured to generate a second signal when released by the user;
- a power supply comprising an internal logic controlled power switch, the power supply in electrical communication with at least the pump motor,
- wherein the internal logic controlled power switch includes an active state and an inactive state, and
- wherein the active state and the inactive state are switchable;
- an overspeed detector in electrical communication with at least the pump motor and a hall position sensor, the overspeed detector configured to generate a first overspeed signal, the overspeed detector further configured to generate a second overspeed signal;
- an under voltage detector in electrical communication with at least the power supply, the under voltage detector configured to measure a logic voltage, the under voltage detector further configured to generate an under voltage disable signal; and
- a pump cartridge detector in electrical communication with at least the pump cartridge, the pump cartridge detector configured to generate a positive pump cartridge signal, the pump cartridge detector further configured to generate a negative pump cartridge signal, wherein the pump cartridge detector is configured to determine whether the pump cartridge is in proper communication with the pump motor,
- where in a pump cartridge piston is forced into a known location by positioning a transmission at a top dead center position before fully inserting the pump cartridge,
- wherein the pump motor is turned to 60 thrusts per minute, enabling an index sensor to detect a position of the pump cartridge piston, and
- wherein, if a piston position is not fully compressed and a pump cartridge motion stops, a user interface generates a warning to the user until the pump cartridge piston is fully compressed.

2. The pump failsafe apparatus of claim 1, further comprising an over temperature switch in electrical communication with at least the overspeed detector, the over temperature switch configured to determine a motor temperature and instruct the pump failsafe apparatus to enter the inactive state if the motor temperature surpasses a predetermined motor temperature threshold.

3. The pump failsafe apparatus of claim 2, wherein the predetermined motor temperature threshold is 75 degrees Celsius.

4. The pump failsafe apparatus of claim 2, further comprising a thermistor configured to monitor the motor temperature.

5. The pump failsafe apparatus of claim 1, further comprising a handpiece sensor in electrical communication with at least the overspeed detector, the handpiece sensor configured to determine whether a handpiece is properly attached and, if the handpiece is not properly attached, to instruct the pump failsafe apparatus to enter the inactive state.

6. The pump failsafe apparatus of claim 1, wherein the first signal immediately disables the overspeed detector, and wherein the second signal, generated upon release of the foot pedal, includes a delay, enabling the pump motor to slow from a first speed to a second speed.

7. The pump failsafe apparatus of claim 1, wherein the pump cartridge detector is an optical sensor.

8. The pump failsafe apparatus of claim 1, wherein the pump motor is a brushless DC motor, and wherein the pump motor is in electrical communication with a motor driver, the motor driver configured to transfer power from the power supply to the pump motor.

9. The pump failsafe apparatus of claim 8, wherein the motor driver is further configured to convert a computer speed signal and signals from the hall position sensor into an AC voltage.

10. A pump failsafe apparatus for use with a pump motor, the pump failsafe apparatus comprising:
- a pump cartridge configured to connect to the pump motor;
- a foot pedal configured to generate a first signal when depressed by a user, the foot pedal further configured to generate a second signal when released by the user;
- a power supply comprising an internal logic controlled power switch, the power supply in electrical communication with at least the pump motor,
- wherein the internal logic controlled power switch includes an active state and an inactive state, and
- wherein the active state and the inactive state are switchable;
- an overspeed detector in electrical communication with at least the pump motor and a hall position sensor, the overspeed detector configured to generate a first overspeed signal, the overspeed detector further configured to generate a second overspeed signal;
- an under voltage detector in electrical communication with at least the power supply, the under voltage detector configured to measure a logic voltage, the under voltage detector further configured to generate an under voltage disable signal;
- a pump cartridge detector in electrical communication with at least the pump cartridge, the pump cartridge detector configured to generate a positive pump cartridge signal, the pump cartridge detector further configured to generate a negative pump cartridge signal; and
- wherein the first signal immediately disables the overspeed detector, and wherein the second signal, generated upon release of the foot pedal, includes a delay, enabling the pump motor to slow from a first speed to a second speed.

11. The pump failsafe apparatus of claim 10, further comprising an over temperature switch in electrical communication with at least the overspeed detector, the over temperature switch configured to determine a motor temperature and instruct the pump failsafe apparatus to enter the inactive state if the motor temperature surpasses a predetermined motor temperature threshold.

12. The pump failsafe apparatus of claim 11, wherein the predetermined motor temperature threshold is 75 degrees Celsius.

13. The pump failsafe apparatus of claim 11, further comprising a thermistor configured to monitor the motor temperature.

14. The pump failsafe apparatus of claim 10, further comprising a handpiece sensor in electrical communication with at least the overspeed detector, the handpiece sensor configured to determine whether a handpiece is properly attached and, if the handpiece is not properly attached, to instruct the pump failsafe apparatus to enter the inactive state.

15. The pump failsafe apparatus of claim 10, wherein the pump cartridge detector is configured to determine whether the pump cartridge is in proper communication with the pump motor,
- wherein a pump cartridge piston is forced into a known location by positioning a transmission at a top dead center position before fully inserting the pump cartridge,
- wherein the pump motor is turned to 60 thrusts per minute, enabling an index sensor to detect a position of the pump cartridge piston, and
- wherein, if a piston position is not fully compressed and a pump cartridge motion stops, a user interface generates a warning to the user until the pump cartridge piston is fully compressed.

16. The pump failsafe apparatus of claim 15, wherein the pump cartridge detector is an optical sensor.

17. The pump failsafe apparatus of claim 10, wherein the pump motor is a brushless DC motor, and wherein the pump motor is in electrical communication with a motor driver, the motor driver configured to transfer power from the power supply to the pump motor.

18. The pump failsafe apparatus of claim 17, wherein the motor driver is further configured to convert a computer speed signal and signals from the hall position sensor into an AC voltage.

* * * * *